US008335555B2

(12) United States Patent
Lehman

(10) Patent No.: US 8,335,555 B2
(45) Date of Patent: Dec. 18, 2012

(54) RADIAL REFLECTION DIFFRACTION TOMOGRAPHY

(75) Inventor: Sean K. Lehman, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1171 days.

(21) Appl. No.: 10/814,435

(22) Filed: Mar. 30, 2004

(65) Prior Publication Data

US 2004/0254463 A1      Dec. 16, 2004

Related U.S. Application Data

(60) Provisional application No. 60/474,861, filed on May 30, 2003.

(51) Int. Cl.
*A61B 5/05* (2006.01)

(52) U.S. Cl. ........ 600/424; 600/407; 600/437; 600/439; 600/465; 600/473

(58) Field of Classification Search ................. 600/407, 600/410, 437, 473, 424, 439, 465, 474
See application file for complete search history.

(56) References Cited

U.S. PATENT DOCUMENTS

| 4,852,577 | A | | 8/1989 | Smith et al. | |
|---|---|---|---|---|---|
| 5,305,752 | A | | 4/1994 | Spivey et al. | |
| 5,353,798 | A | * | 10/1994 | Sieben | 600/462 |
| 5,417,218 | A | | 5/1995 | Spivey et al. | |
| 5,435,312 | A | | 7/1995 | Spivey et al. | |
| 5,492,121 | A | | 2/1996 | Lu | |
| 5,522,392 | A | * | 6/1996 | Suorsa et al. | 600/454 |
| 5,581,144 | A | | 12/1996 | Corl et al. | |
| 5,725,494 | A | | 3/1998 | Brisken | |
| 5,906,580 | A | | 5/1999 | Kline-Scholder et al. | |
| 6,221,015 | B1 | | 4/2001 | Yock | |
| 6,246,898 | B1 | * | 6/2001 | Vesely et al. | 600/424 |
| 6,283,920 | B1 | | 9/2001 | Eberle et al. | |
| 6,283,921 | B1 | | 9/2001 | Nix et al. | |
| 6,592,526 | B1 | * | 7/2003 | Lenker | 600/463 |
| 2002/0157472 | A1 | | 10/2002 | Stephens et al. | |
| 2003/0199767 | A1 | * | 10/2003 | Cespedes et al. | 600/473 |
| 2003/0199768 | A1 | * | 10/2003 | Cespedes et al. | 600/473 |
| 2003/0236443 | A1 | * | 12/2003 | Cespedes et al. | 600/29 |

OTHER PUBLICATIONS

Michael J. Davies, MD, Stability and Instability: Two Faces of Coronary Atheroscleroiss, The Paul Dudley White Lecture 1995. *Circulation 1996*; 04:2013-2020.
R. Lee et al., "The Unstable Atheroma". *Arteriosclerosis, Thrombosis and Vascular Research Biol.* 1997;17:1859-1867.

(Continued)

*Primary Examiner* — Brian Casler
*Assistant Examiner* — Joel Lamprecht
(74) *Attorney, Agent, or Firm* — John P. Wooldridge

(57) ABSTRACT

A wave-based tomographic imaging method and apparatus based upon one or more rotating radially outward oriented transmitting and receiving elements have been developed for non-destructive evaluation. At successive angular locations at a fixed radius, a predetermined transmitting element can launch a primary field and one or more predetermined receiving elements can collect the backscattered field in a "pitch/catch" operation. A Hilbert space inverse wave (HSIW) algorithm can construct images of the received scattered energy waves using operating modes chosen for a particular application. Applications include, improved intravascular imaging, bore hole tomography, and non-destructive evaluation (NDE) of parts having existing access holes.

31 Claims, 4 Drawing Sheets

OTHER PUBLICATIONS

Zahi A. Fayad, PhD. et al, "In Vivo Magnetic Resonance Evaluation of Atherosclerotic Plaques in the Human Thoracic Aorta. A Comparison with Transesophageal Echocardiography", Zena and Michael A. Wiener Cardiovascular Institute. *Circulation 101*:2503-2509, 2000.

M. O'Donnell et al, "Catheter Arrays: Can Intravascular Ultrasound Make a Difference in Managing Coronary Artery Disease". *IEEE Ultrasonics Symposium*, pp. 1447-1456, 1997.

L. Gatzoulis, et al, "Scanning Techniques for Three-Dimensional Forward-Viewing Intravascular Ultrasound Imaging". *Ultrasound Med. & Biol.*, vol. 26, No. 9, pp. 1461-1474, 2000.

S. Wickline et al, "Beyond Intravascular Imaging: Quantitative Ultrasonic Tissue Characterization of Vascular Pathology". *IEEE Ultrasonics Symp 1994*, pp. 1589-1597. *IEEE*, 1994.

P. Yock et al, "Intravascular Ultrasound: Looking Below the Surface of Vascular Disease". *Circulation*, 81:1715-1718, 1990.

M. Kaveh et al, "Signal Processing for Diffraction Tomography". *IEEE Transactions on Sonics and Ultrasonics*, vol. SU-31:231-239, No. 4, Jul. 1984.

T. Mast, "Wideband Quantitative Ultrasonic Imaging by Time-Domain Diffraction Tomography". *J. Acoust, Society of America*, 106:3061-3071, 1999.

S. Jespersen et al, "In Vitro Spatial Compound Scanning for Improved Visualization of Atherosclerosis". *Ultrasound in Med. & Biol.*, vol. 26, No. 8, pp. 1357-1362, 2000.

C. De Korte et al, Intravascular Elasticity Imaging Using Ultrasound: Feasibility Studies in Phantoms. *Ultrasound in Medicine and Biology*, vol. 23, No. 5, pp. 735-746, 1997.

C. De Korte et al, "Characterization of Plaque Components with Intravascular Ultrasound Elastography in Human Femoral and Coronary Arteries in Vitro." *Circulation*, 102:617-623, 2000.

\* cited by examiner

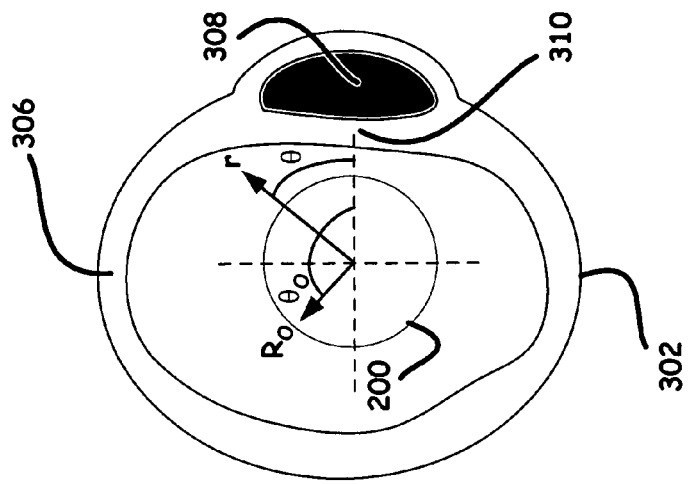
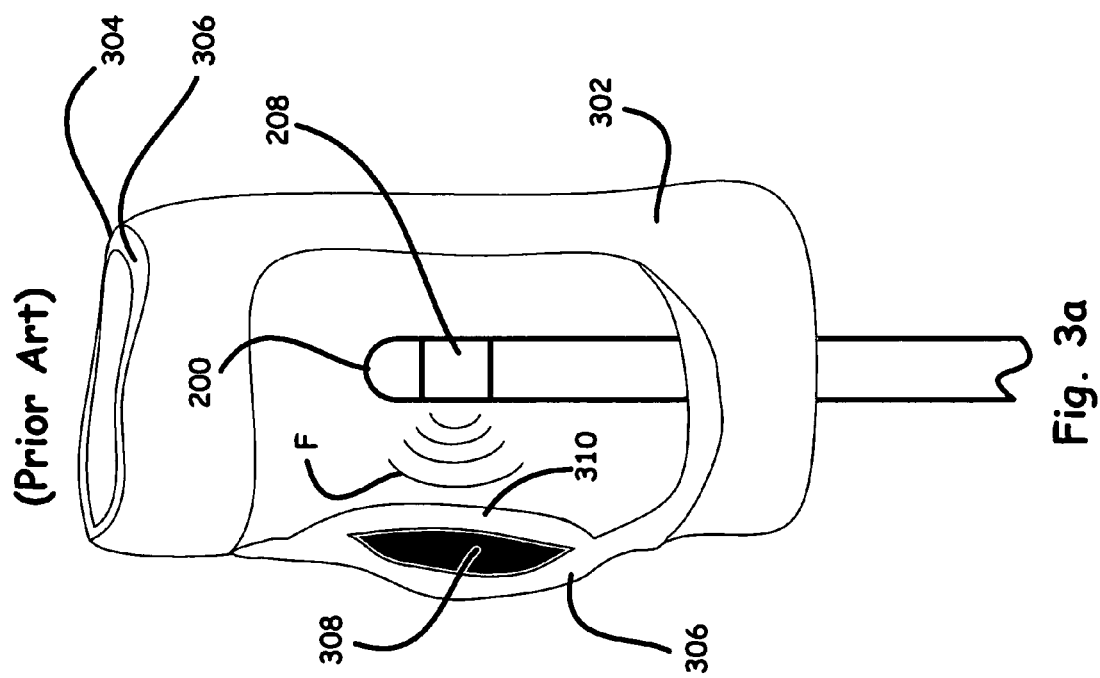
Fig. 3b
Fig. 3a (Prior Art)

RADIAL REFLECTION DIFFRACTION TOMOGRAPHY

RELATED APPLICATION

This application claims the benefit of U.S. Provisional Application No. 60/474,861, filed May 30, 2003, entitled, "Radial Reflection Diffraction Tomography," which is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates in general to imaging, and more particularly to an imaging method and apparatus employing Radial Reflection Diffraction Tomography.

2. Description of Related Art

Intravascular ultrasound (IVUS) imaging provides a method for imaging the interior of blood vessel walls. In standard acoustical techniques, a catheter with a rotating ultrasound transducer is inserted into a blood vessel. The transducer launches a pulse and collects the reflected signals from the surrounding tissue. Conventional ultrasonic imaging systems use B-mode tomography or B-scans, wherein images are formed from the envelope of the received display echoes returning to an ultrasonic transducer as brightness levels proportional to the echo amplitude and by assuming straight ray theory (i.e., geometrical optics). The brightness levels can then be used to create cross-sectional images of the object in the plane perpendicular to the transducer image. However, such images typically suffer from the consequences of ray theory of sound propagation, which does not model its wave nature.

A circumferential scan can be made by either rotating a single transducer (mechanical beam steering) or by phasing an array of transducers around a circumference (electronic beam forming). Typically, one ultrasound pulse is transmitted and all echoes from the surface to the deepest range are recorded before the ultrasound beam moves on to the next scan line position where pulse transmission and echo recording are repeated. When utilizing B-scan, the vertical position, which provides depth of each bright dot is determined by the time delay from pulse transmission to return of the corresponding echo, and the horizontal position by the location of the receiving transducer element.

Although B-scan IVUS images can be utilized to detect plaque and characterize its volume, the classification of plaque types by ultrasound is very difficult. Conventional B-scan images utilizes scattering, which, in turn, depends on the acoustic impedance dissimilarity of tissue types and structures. Although hard calcifications in some plaque can be detected using such a mismatch, the similarity in the acoustic properties of fibrous plaque and lipid pools prevents direct identification. Consequently, the size of the fibrous cap cannot be accurately estimated.

Diffraction tomography has additionally been applied to medical imaging problems for a number of years, usually in a standard circumferential through transmission mode. Furthermore, improved vascular images have been provided by utilizing time domain diffraction tomography, a technique capable of accounting for the wave propagation of the transmitted acoustic waves in addition to redundant information from multiple angular views of the objects imaged. A related B-mode approach that incorporates spatial compounding has also been employed to provide improved vascular images through multiple look angles.

Background information on rotational IVUS systems are described, for example, in U.S. Pat. No. 6,221,015 to Yock. Background information on phased-array IVUS systems are described, for example, in U.S. Pat. No. 6,283,920 to Eberle et al., as well as U.S. Pat. No. 6,283,921 to Nix et al. Multifunctional devices have been proposed in other areas of vascular intervention. For example, U.S. Pat. No. 5,906,580 to Kline-Schoder et al., describes an ultrasound transducer array that may transmit signals at multiple frequencies and may be used for both ultrasound imaging and ultrasound therapy. Therapeutic ultrasound catheters, are described, for example, in U.S. Pat. No. 5,725,494 to Brisken et al. and U.S. Pat. No. 5,581,144 to Corl et al., which describes another ultrasound transducer array that is capable of operating at multiple frequencies. However, none of the above devices and associated techniques from the above cited patents, are suited for rapid identification of objects, such as, but not limited to, vulnerable plaque or objects recessed in a bore hole, in accordance with the principles of the present invention.

SUMMARY OF THE INVENTION

The present invention is directed to a wave-based imaging method, which includes: directing predetermined energy waves radially outward from within an interspace and receiving scattered energy waves from one or more objects. The received data are processed to produce images of the objects, wherein the processing includes application of a wave-based algorithm that can map an angular location and a plurality of frequency parameters of the received scattered energy waves to construct images of the one or more objects.

Another aspect of the present invention is directed to a wave-based imaging method that can be utilized to characterize a plaque, which includes: inserting a catheter having a longitudinal axis and a distal end into an artery, wherein the catheter further includes a single transmitter disposed about the distal end of the catheter and a receiver aperture having a plurality of receivers additionally disposed about the distal end of the catheter, wherein the transmitter and the receiver aperture is capable of rotating up to 360 degrees about the longitudinal axis of the catheter. As part of the method, one or more predetermined energy waves are directed radially outward from the single transmitter and radial scattered energy waves are received in a predetermined imaging mode by the receiver aperture. The received scattered energy waves results in collected data capable of being processed to produce images of plaque from the surrounding artery walls, wherein the processing includes application of a wave-based algorithm that can map an angular location and a plurality of frequency parameters of the received scattered energy waves to construct the images and determine the risk of rupture and/or thrombosis.

Another aspect of the present invention is directed to a wave-based imaging method that can be utilized to characterize a plaque, which includes: inserting a catheter into an artery, directing one or more predetermined energy waves radially outward and receiving one or more radial scattered energy waves from a distal end of the catheter; collecting a radial scattered tomographic data baseline of the artery's tissue; measuring an applied external pressure to the artery; obtaining a deformation radial scattered tomographic data set of the artery's tissue after application of the external pressure; and processing the radial scattered tomographic data baseline and the deformation radial scattered tomographic data set to produce a final image indicating elasticity of the artery to characterize the imaged plaque, wherein the processing includes application of a wave-based algorithm that can map an angular location and a plurality of frequency parameters of the received scattered energy waves.

A further aspect of the present invention is directed to a wave-based imaging apparatus, which includes a flexible substrate having a longitudinal axis and a distal region and one or more elements disposed on the distal region and capable of directing one or more predetermined energy waves radially outward and receiving one or more radial scattered energy waves from one or more objects. The received scattered energy waves are capable of producing images of one or more objects by processing a collected data set, wherein the processing includes application of a wave-based algorithm that can map an angular location and a plurality of frequency parameters of the received scattered energy waves.

A final aspect of the present invention is directed to a wave-based imaging apparatus that includes a Hilbert space inverse wave (HSIW) algorithm that can map an angular location and a plurality of frequency parameters of said received reflected diffracted energy waves so as to characterize plaque within a living vessel.

Accordingly, the present system and method employs desired Radial Reflection Diffraction Tomographic techniques to determine the state and location of buried wastes, to track plumes of underground contaminants of materials, to determine the state of materials residing in waste drum barrels or weapons, to evaluate nondestructively parts having existing access holes (e.g., automobile parts), and for identifying potentially life threatening vulnerable plaque buildup on living vessel walls.

BRIEF DESCRIPTION OF THE DRAWINGS

FIG. 3a shows a conventional IVUS catheter inserted into a diseased artery.

FIG. 3b illustrates the RRDT geometry of the present invention when a catheter is inserted into a diseased artery.

DETAILED DESCRIPTION OF THE INVENTION

Referring now to the following detailed information, and to incorporated materials; a detailed description of the invention, including specific embodiments, is presented.

Unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contains certain errors necessarily resulting from the standard deviation found in their respective testing measurements.

General Description

The present invention employs inverse wave techniques to reconstruct images of a medium surrounding a physical probe in a plane perpendicular to an axis of rotation in a radial reflection configuration, i.e., in a multimonostatic or a multistatic arrangement disclosed infra, wherein one or more transmitting and receiving elements, more often at least about 15 of such elements, e.g., transducer(s), are at a fixed radius and designed to collect scattered fields, e.g., reflected and diffracted fields. Such a radial reflection diffraction tomography (RRDT) technique is based upon a linearized scattering model to form images given the disclosed physical transmitter and receiver configurations and the mathematical method, i.e., a Hilbert-based wave algorithm, utilized to invert the scattering collected fields.

As example embodiments, the multimonostatic and multistatic probes can be mounted at the end of a flexible substrate, such as a catheter or snaking tube that can be inserted into a part with an existing access hole or a medium (e.g., an artery) with the purpose of forming images of the plane perpendicular to the axis of rotation. By applying the Hilbert space inverse wave (HSIW) algorithm of the present invention to the collected data of such multimonostatic and multistatic probes, radial reflected diffraction tomographic images are readily obtained.

Specific Description

Figure 1A:
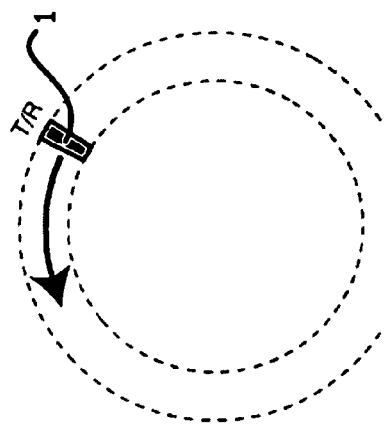
FIG. 1a illustrates a basic multimonostatic mode configuration that includes a single transducer rotating about a fixed center.

FIG. 1(a) shows a basic multimonostatic conceptual arrangement of the present invention, wherein a single energy source element 1, such as a transducer, can operate as both source and receiver (as denoted by T/R, to indicate transmitter and receiver) at multiple spatial locations. At each angular location along the illustrated dashed circumference, as denoted by the directional arrow, energy source element 1 can launch a primary field wave (not shown) and receive a reflected scattered field wave (not shown). Such an arrangement often requires a spectrally wide band frequency diverse source capable of producing frequencies from about 1 kHz to about 3 THz (Electromagnetic frequencies), often from about 100 Hz to about 10 GHz (Acoustic frequencies), more often between about 20 MHz and about 60 MHz (Acoustic frequencies), to provide spatial diversity so as to form images of a surrounding medium.

Figure 1B:
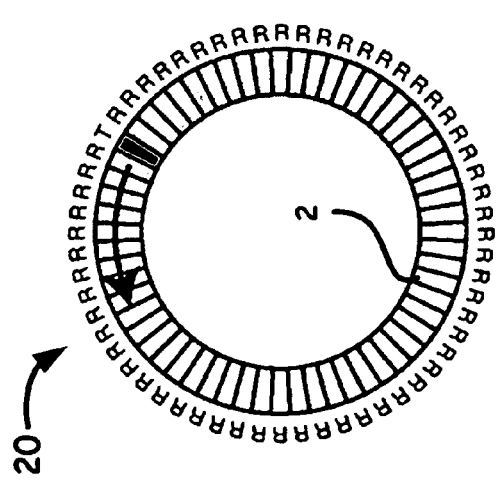
FIG. 1b illustrates a basic multistatic mode configuration that includes a fixed annular array of outwardly directed transducers.

FIG. 1(b) shows an example conceptual multistatic mode embodiment, wherein a plurality of fixed energy source elements 2, e.g., transducers, are arranged as an annular array, generally designated by the reference numeral 20. In succession, along for example, the illustrated directional arrow, each energy source element (for example, the element denoted by the letter T to indicate a transmitter) is capable of launching a primary field wave (not shown) and a backscattered field wave (not shown) is measured on all the remaining elements (as denoted by the letter R, indicating the remaining fixed elements are operating as receivers).

Figure 1C:
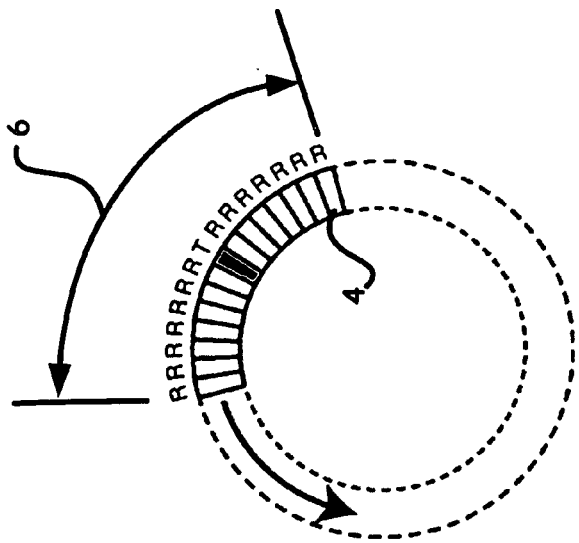
FIG. 1c illustrates a basic multistatic mode configuration that includes a rotating aperture.

FIG. 1(c) illustrates a beneficial multistatic conceptual arrangement that includes a plurality of energy source elements 4 configured in a rotating sub-aperture 6, as denoted by the bi-directional arrow, formed by a single transmitter, as denoted by the letter T to indicate a transmitter, and surrounded by multiple receivers, as denoted by the letter R. At each angular location, as denoted by the single directional arrow along the illustrated dashed circumference, transmitter T can launch a primary field (not shown) and a backscattered field (not shown) is measured on all receivers R.

When operating in a reflection mode as disclosed herein, the mathematics applied to the collected data operate beneficially to image objects because the range resolution of the reconstructed image is proportional to the number of frequencies used in the reconstruction. Under the Hilbert space inverse wave algorithm, increasing the number of frequencies and transducers, increases the complexity of the reconstruction, the size of the intermediary data files, reconstruction time, and computer memory requirement. Thus, the trade-off between computer resources and resolution is a consideration. Nonetheless, the techniques employed in the present invention are beneficial even at acoustic frequencies from as low as about 100 Hz to as high as about 10 GHz. Such lower frequencies allow the disclosed embodiments to additionally be employed in borehole type of applications, such as, but not limited to, characterizing underground contamination plumes or waste in contamination barrels.

For either the multimonostatic or multistatic example embodiments, the planar reconstruction of the imaged object(s) requires that the one or more collected measurements map a pair of spatial variables (i.e., angular location and incident source frequency) of a physical object into the angular location and frequency parameters of the measured field.

An exemplary application of the present invention is in the characterization of vulnerable atherosclerotic plaque. Arthrosclerosis is a condition where the arteries are obstructed by the buildup of deposits, "intravascular plaque" (IVP), on the inside of arterial walls and such a buildup of deposits can lead to what is known to those of ordinary skill in the art as cerebrovascular disease, which is the third leading cause of death and the leading cause of major disability among adults. Plaque grows as a fibrous tissue encapsulating a lipid pool and as the plaque grow it may incorporate calcium. Of particular concern is vulnerable or unstable plaque because of the possibility of such plaque becoming inflamed and unexpectedly rupturing. Stable or non-vulnerable plaque, typically includes a thick layer of fibrous tissue of about 800 microns but is not life threatening and can be treated slowly. A thin fibrous cap of typically up to about 300 microns covering a pool of a soft lipid core typically characterizes vulnerable plaque. When such a cap is disrupted, the thin cap is compromised and the lipid deposited into the artery can produce adverse effects, such as thrombus formation, strokes and death.

Figure 2:
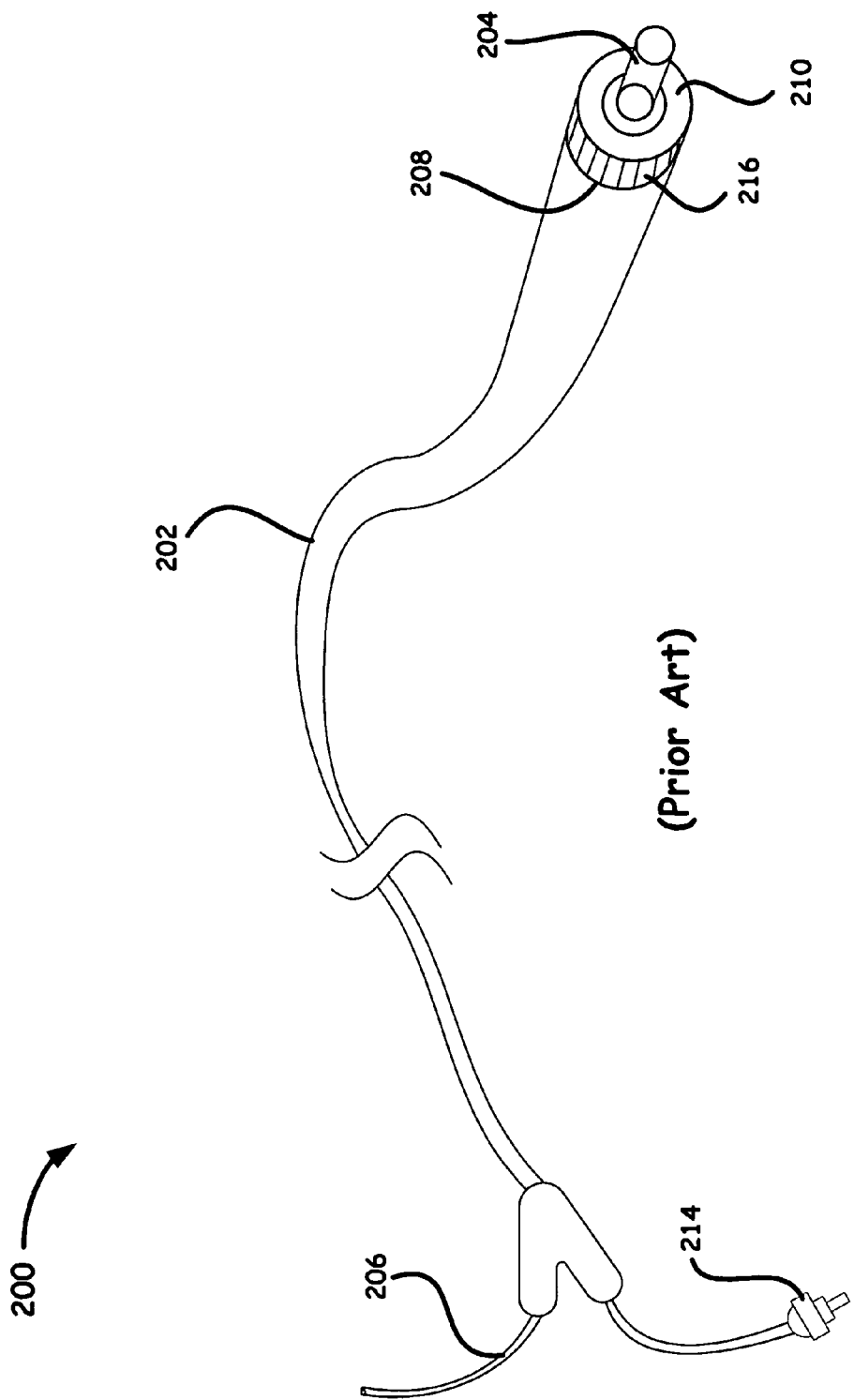
FIG. 2 shows a conventional IVUS catheter.

FIG. 2 shows a conventional catheter, generally designated as reference numeral 200, for intravascular tissue characterization, such as atherosclerotic vulnerable plaque. Such a catheter 200, typically has an elongated flexible substrate 202 with an axially extending lumen 204 through which a guide wire 206, and/or various other devices or other instruments can be delivered to a region of interest. An ultrasonic transducer assembly 208 is provided at the distal end 210 of the catheter, with a connector 214 located at the proximal end of the catheter for transducer manipulation and processing received transducer signals. Transducer assembly 208 can comprise a plurality of transducer elements 216 arranged in a cylindrical array centered about a longitudinal axis 218 of the catheter for transmitting and receiving ultrasonic energy. Adhesive (not shown) and or an end-cap (not shown) can be applied to transducer assembly 208, and lumen 204 to protect such elements from the surrounding environment. Transducer assembly's 208 individual elements (not shown) and conductive acoustical backing (not shown) are often mounted on the inner wall of elongated flexible body 202 operating as the flexible substrate.

FIG. 3a illustrates a typical IVUS method using such a catheter 200, as shown in FIG. 2a. In such a conventional application, catheter 200, having a transducer assembly 208 that can launch an energy wave as a primary field (as denoted by the letter F) is inserted typically non-centered into a nominally circular diseased artery 302. Around a wall 304 of artery 302 is a fibrous collagen plaque 306. A lipid pool 308 can reside inside such a fibrous structure, wherein when a fibrous cap 310 of plaque 306 separating lipid pool 302 from the blood (not shown) within artery 302 is more than about 800 µm thick, plaque 306 is characterized as stable. However, in cases where cap 310 is less than about 300 µm thick, such a plaque is characterized as vulnerable, and is more likely to rupture and/or thrombosis.

The present invention utilizes the disclosed RRDT approach for improved intravascular applications such as characterizing plaque as discussed above, and incorporates various aspects of the method of utilizing a probe, such as, but not limited to, the catheter as shown in FIG. 3a. However, such catheters 200 and similar probes known to those of ordinary skill in the art typically show angular overlap for beam processing, which results in loss of valuable image information of one or more objects of interest within a surrounding medium. The present invention overcomes such processing by incorporating novel improvements of the transmitters and receivers, by utilizing frequencies between about 20 MHz (Acoustic) and about 60 MHz (Acoustic), and by utilizing RRDT techniques of the present invention as discussed herein. Such novel embodiments acccounts for phase, amplitude, and beam diffraction, to recover not only such loss of valuable image information information but to further enhance the imaging capabilities of the invention by providing images with improved lateral resolution of the acoustic absorption and sound speed.

FIG. 3b shows the geometry incorporated by the RRDT method of the present invention. FIG. 3b shows a cross-sectional view of a catheter 200, having an outer diameter between about 0.25 mm and about 5 mm, being inserted into an artery 302, having a surrounding plaque 306 that includes a cap 310 and a lipid pool 308. Inserted into artery 302 is a non-centered catheter 200, which includes a transducer assembly (not shown) that can be disposed about the distal end of catheter 200, as disclosed in the present invention, with a radial location specified by $r_O \equiv R_O (\cos \theta_O, \sin \theta_O)$, where $R_O$ is the catheter 200 probe radius, a constant. At each angular location, $\theta_O$, transducer assembly 208, as shown in FIG. 3a, launches a primary field F radially outward (as denoted by the letter r) into a medium, such as the blood (not shown) and surrounding tissue in this example, and the transducer arrangement, as disclosed in the present invention, can measure a reflected scattered field (not shown) having, for example, at least up to about 90 degrees of angular content from one or more objects, such as the linings of cap 310 that overlies lipid pool 308.

As another example embodiment, the RRDT method and apparatus of the present invention can be combined with elastography to gain further insight into a surrounding medium's elastic properties and provide further information in the determination of characterizing plaque as vulnerable or stable. Generally, the contrast in elastic properties between a lipid pool and a fibrous cap is evident. By utilizing elastography, the elastic properties of a vessel wall can be obtained by observing a deformation of the vessel due to an external pressure, such as the pressure produced by a heart. Such a change in the arterial pressure due to the pumping action of the heart produces a measurable deformation of the tissue surrounding the vessel. Such a deformation can be measured by tracking a motion of patterns in successive intravascular scans as disclosed by the present invention. By knowing the arterial pressure and the measured deformation, the present invention can recover elastic properties of the surrounding tissue. From such elastic properties, one can further characterize the surrounding tissue to predict plaque composition.

Figure 4:
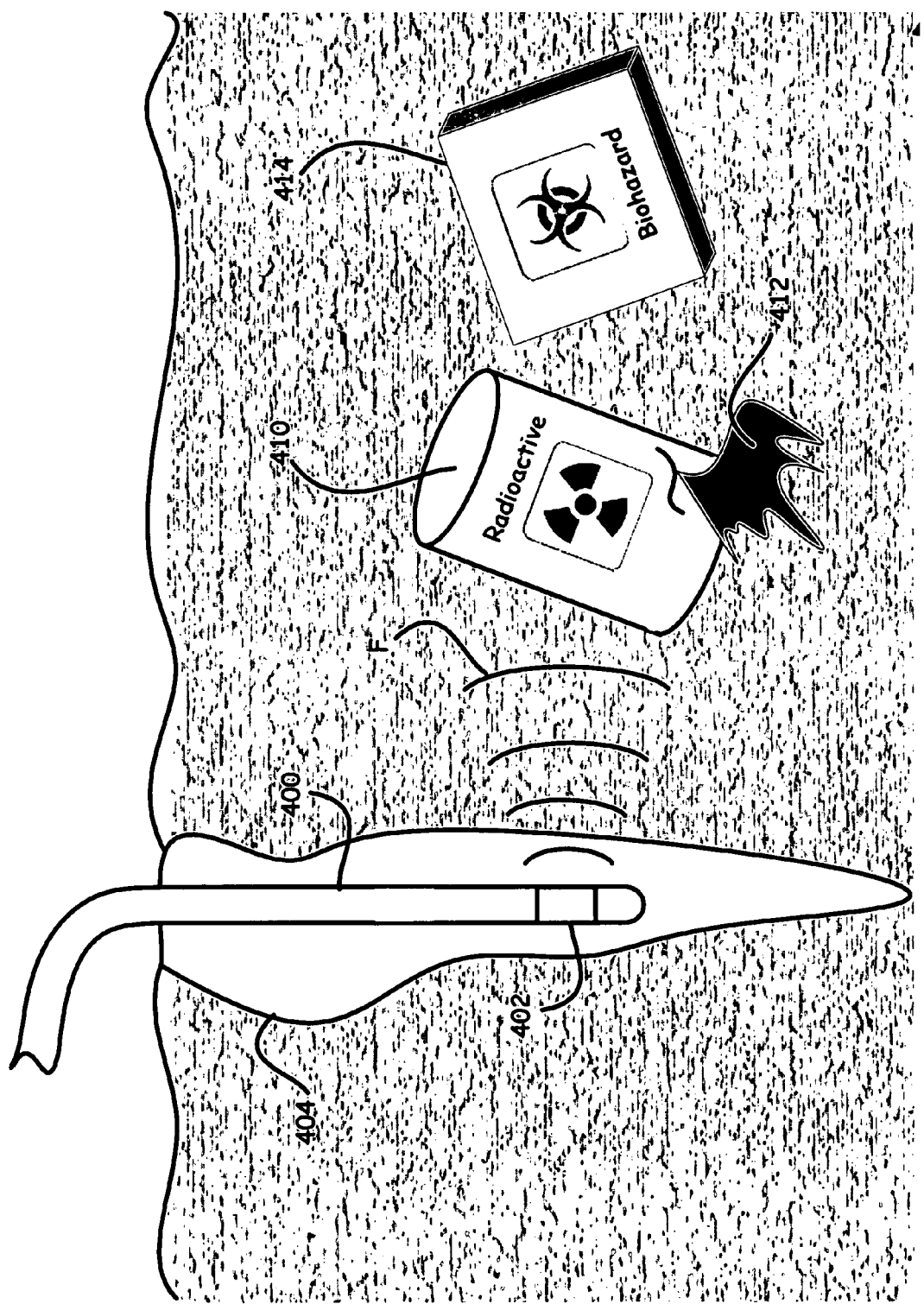
FIG. 4 illustrates RRDT non-destructive evaluation within a bore hole.

FIG. 4 illustrates a further beneficial embodiment, wherein the present invention can be utilized for non-destructive characterization (i.e., RRDT imaging) in applications other than for intravascular RRDT imaging. As shown by the example cross-sectional underground view of a borehole 404 in FIG. 4, a flexible substrate 400 or snake-like tube having a transducer assembly 402 similarly configured like the intravascular RRDT application discussed above, can be lowered into bore hole 404 so as to image a site using RRDT techniques. Such an arrangement can launch a primary field (denoted by the letter F) and receive diffracted energy waves having frequencies often between about 100 Hz and about 300 Hz, to determine the state of buried wastes, such as waste within a radioactive waste drum barrel 410 or a biohazardous container, and/or to track a plume 412 of underground contaminants. In a similar manner, disclosed probes herein, can be inserted into waste drum barrels 410, or weapons (not shown) or any part having an existing access hole, such as, but not limited to, an automobile engine, and determine the state of the part or material.

Hilbert Space Wave Inversion

Hilbert spaces are spaces constructed using vectors. Specifically they define vector spaces where sets of vectors in the space "add up" to another vector, an analog to Euclidean space where measurements can be added to result in another valid measurement. Hilbert spaces are particularly useful when studying the Fourier expansion of a particular function. In the Fourier transform, a complex function describing a waveform is re-expressed (transformed) into the sum of many simpler wave functions. A Hilbert space describes the "universe of possible solutions" given one particular such function. The Hilbert space inverse wave (HSIW) algorithm of the present invention enables an inverse for any multistatic or multimonostatic geometry with any combination of sources, receivers, and frequencies.

In a radial reflection device of the present invention, such as an intravascular ultrasound probe having an outer diameter between about 0.25 mm and about 5 mm, or a probe configured to non-destructively characterize buried wastes (e.g., tracking plumes of underground contaminants of materials), evaluating the state of materials residing in waste drum barrels or weapons, or to non-destructively evaluate parts with existing access holes (e.g., automobile parts), acquired data are collected at discrete angular locations. Such angular locations are denoted by:

$$R_n^t = R_0(\cos\theta_n, \sin\theta_n) \quad (1)$$

for transmitter locations, where $\theta_n = n\Delta\theta_{src}$ for $n=0,1\ldots,N_{src}-1$, where $N_{src} 2\pi/\Delta\theta$, and $\Delta\theta_{src}$ is the source angular increment.

Similarly, receiver locations are given by:

$$R_m^r = R_o(\cos\theta_m, \sin\theta_m) \quad (2)$$

where $\theta_m = m\Delta\theta_{rcv}$ for $m=0,1\ldots,N_{src}-1$, where $N_{rcv} 2\pi/\Delta\theta_{rcv}$, and $\Delta\theta_{rcv}$ is the receiver angular increment.

For each source, configured receiver(s) can record a backscattered field as a time series that can be digitized for processing. Discrete Fourier transforming the time series data result in the spectrum of one or more measured wave forms at discrete frequencies. The forward scattering equation under the Born approximation with both spatial and frequency diversity is given by:

$$\psi_B^{scat}(R_m^r, R_n^t, \omega_l) = P(\omega_l) k_O^2(\omega_l) \int dr' G(R_m^r, r', \omega_l) o(r') G(r', R_n^t, \omega_l), \quad (3)$$

where $\omega_l, l=0,1\ldots,N_f-1$ are the discrete frequencies and $N_f$ is the number of frequencies in the pulse band width.

The HSIW as disclosed herein interprets Equation (3) as a mapping from a continuous object space to a discrete measurement space. The object space is the physical (x,y) space of the object function. The measurement space includes discrete angles and temporal frequencies at which the scattered data are collected. The scattering operator projects the object onto the measurement space. The forward propagation or projection kernel is defined as:

$$\Pi^*(r) = P(\omega_l) k_O^2(\omega_l) G(R_m^r, r, \omega_l) G(r, R_n^t, \omega_l), \quad (4)$$

where $\Pi(r)$ is a $J \equiv (N_{src} \times N_{rcv} \times N_f)$ element column vector, and $P(\omega_l)$ is the incident pulse spectrum. Mathematically, the projection is represented as an inner product between the object function and the kernel via:

$$D = \int dr \Pi^*(r) o(r) = <\Pi, o>, \quad (5)$$

where D is a J element column vector, and where each element represents a particular source, receiver, and frequency combination. Symbolically, the forward scattering operator, K, is defined as:

$$K[\bullet] \equiv \int dr \Pi^*(r)[\bullet]. \quad (6)$$

The HSIW method of the present invention is employed to derive an inverse of the operator as shown in equation (6). The singular value decomposition (SVD) of K is given as:

$$K = USV^\dagger, \quad (7)$$

where the columns of U form an orthonormal set of column vectors, $u_j$, which span a measured data space, and the components of V form an orthonormal set of vectors, $v_j(r)$, which span an object space. S is a diagonal matrix of singular values, $\sigma_j$. It is emphasized that the $u_j$ are complex column vectors where as the $v_j(r)$ are complex functions of r. The set of normal equations for such a singular system are:

$$K v_j(r) = \sigma_j u_j, \quad (8)$$

$$K^\dagger u_j = \sigma_j v_j(r), \quad (9)$$

$$K K^\dagger u_j = \sigma_j K v_j(r) = \sigma_j^2 u_j, \quad (10)$$

$$K^\dagger K v_j(r) = \sigma_j K^\dagger u_j(r) = \sigma_j^2 v_j(r), \quad (11)$$

The inversion method of the present invention estimates the object function of equation (5) given measured data in D. Such an inversion incorporates expanding the object function in terms of $v_j(r)$:

$$\hat{o}(r) = \sum_{j=0}^{J-1} \alpha_j v_j(r), \quad (12)$$

where the $\alpha_j$ are constant coefficients to be determined. Substituting the object expansion into equation (5) results in:

$$D = \int dr \Pi^*(r) \sum_{j=0}^{J-1} \alpha_j v_j(r) = \sum_{j=0}^{J-1} \alpha_j \int dr \Pi^*(r) v_j(r), \quad (13)$$

Applying the definition of the K operator in equation (6) to equation (8) yields an expression for the integral of equation (13), $$Kv_j = \int dr \Pi^*(r) v_j(r) = \sigma_j u_j, \tag{14}$$

which reduces equation (13) to:

$$D = \int \sum_{j=0}^{J-1} \alpha_j \sigma_j u_j, \tag{15}$$

Using the orthogonality of the $u_j$ vectors, the unknown $\alpha_j$ is solved as follows:

$$u_i^\dagger D = \sum_{j=0}^{J-1} \alpha_j \sigma_j u_i^\dagger u_j = \sum_{j=0}^{J-1} \alpha_j \sigma_j \delta_{ij} = \alpha_i \sigma_i, \tag{16}$$

resulting in:

$$\alpha_i = \frac{u_i^\dagger D}{\sigma_i}, \tag{17}$$

The adjoint of the forward scattering operator, $K^\dagger$ and the singular values and singular vectors, $\sigma_j$, $u_j$, and $v_j(r)$ are now required. First, the following inner product equation defines the adjoint, $$<u, Kv> = <K^\dagger u, v>, \tag{18}$$

Using the definition of the forward scattering operator from equation (16) results in:

$$u^\dagger \int dr \Pi^*(r) v(r) = \int dr (u^\dagger \Pi^*(r)) v(r), \tag{19}$$

By comparing the right hand sides of equations (18) and (19), the following definition of the adjoint of the forward scattering operator is obtained:

$$K^\dagger[\bullet] = [\bullet] \cdot \Pi^T(r). \tag{20}$$

The $\sigma_j$ and $u_j$ are determined by solving the eigenvalue equation of equation (10) formed by the outer product of the forward scattering operator with its adjoint. Explicitly, the outer product is represented by:

$$(\int dr \Pi^*(r) \Pi^T(r)) u_j = \sigma_j^2 u_j, \tag{21}$$

which is a J×J eigenvalue equation of the form $Ax = \lambda x$. The $\Pi(r)$ vectors are known analytically and can be evaluated numerically. It follows that the elements of the outer product matrix can be computed numerically and the resulting system solved numerically for the $\sigma_j^2$ and $u_j$. Given these and using equation (19) to solve for $v_j(r)$ results in:

$$v_j(r) = \frac{1}{\sigma_j} \Pi^T(r) u_j. \tag{22}$$

Substituting equations (17) and (22) into equation (12) yields the final expression for the reconstruction:

$$\hat{o}(r) = \sum_{j=0}^{J-1} \frac{1}{\sigma_j^2} \Pi^T(r) u_j u_j^\dagger D. \tag{23}$$

As described above, the $\Pi(r)$ vectors of equation (4), and outer products and eigenvalues of equation (21) are computed numerically. The measurement system of the analytically described invention only measures part of the scattered field due to the aperture and the loss of the evanescent field information and accordingly, some of the eigenvalues, $\sigma_j^2$, are close to zero. Those eigenvalues and their corresponding eigenvectors determine the rank of the outer product matrix, and they must not be used in the reconstruction of equation (23). Thus, in the method of the present invention, a Best Rank N approximation is used to select the number of singular values/vectors. A ratio is computed as follows:

$$R(N) = \frac{\sum_{j=0}^{N-1} \sigma_j^2}{\sum_{j=0}^{J-1} \sigma_j^2}, \tag{24}$$

where the singular values are assumedly arranged from smallest to largest: $\sigma_0^2 \leq \sigma_1^2 \leq \sigma_{J-1}^2$. Plotting R(N), the point at which the function starts to rise rapidly is graphically identified. The index of the singular value at which this occurs is labeled as $J_0$. With this value determined, a final reconstruction is as follows:

$$\hat{o}(r) = \sum_{j=J_0}^{J-1} \frac{1}{\sigma_j^2} \Pi^T(r) u_j u_j^\dagger D \tag{25}$$

The HSIW as disclosed herein is flexible in that it allows any transducer configurations of the present invention and any number of frequencies to be used in forming such a final reconstruction.

Changes and modifications in the specifically described embodiments can be carried out without departing from the scope of the invention, which is intended to be limited only by the scope of the claims.

The invention claimed is:

1. A wave-based imaging method, comprising:
   directing from within an interspace, one or more predetermined energy waves radially outward along a predetermined axis;
   receiving in a predetermined imaging mode, one or more radial scattered energy waves from one or more objects; and
   processing said received one or more radial scattered waves, wherein said processing includes application of a wave-based algorithm that can map an angular location and a plurality of frequency parameters of said received scattered energy waves to construct images of said one or more objects, wherein said wave-based algorithm comprises a Hilbert space inverse wave (HSIW) algorithm.

2. The method of claim 1, wherein said-radial scattered energy waves are received by a single rotating radially outward oriented transducer capable of rotating up to 360 degrees about a predetermined axis.

3. The method of claim 1, wherein the step of directing utilizes a single transmitter and wherein the step of receiving utilizes a receiver aperture comprising a plurality of receivers, wherein said transmitter and said receiver aperture are capable of rotating up to 360 degrees about a predetermined axis.

4. The method of claim 2, wherein said transducer is positioned at a distal end portion of a catheter for transmitting and receiving predetermined energy wave frequencies.

5. The method of claim 3, wherein at a predetermined angular imaging location, said receiver aperture is configured to receive up to 90-degrees of angular content resulting from said one or more radial scattered energy waves.

6. The method of claim 3, wherein said single transmitter and said receiver aperture are positioned at a distal end portion of a flexible substrate for transmitting and receiving ultrasonic energy wave frequencies.

7. The method of claim 1, wherein said images are formed along a plane perpendicular to a predetermined axis of rotation.

8. The method of claim 1, wherein said energy waves further comprise acoustic frequencies having a range between 20 MHz and 60 MHz.

9. The method of claim 1, wherein said energy waves further comprise acoustic frequencies having a range between 100 Hz and 10 GHz.

10. The method of claim 1, wherein said energy waves further comprise electromagnetic frequencies having a range between 1 kHz and 3 THz.

11. The method of claim 1, wherein said interspace includes a living vessel.

12. The method of claim 1, wherein said interspace includes a bore hole.

13. A wave-based imaging method of characterizing a plaque, comprising:
inserting a catheter having a longitudinal axis and a distal end into an artery, wherein said catheter further comprises a single transmitter disposed about said distal end of said catheter and a receiver aperture further comprising a plurality of receivers additionally disposed about said distal end of said catheter, wherein said transmitter and said receiver aperture are capable of rotating up to 360 degrees about said longitudinal axis of said catheter;
directing one or more predetermined energy waves radially outward from said single transmitter;
receiving in a predetermined imaging mode, one or more radial scattered energy waves by said receiver aperture; and
processing said received one or more radial scattered energy waves, wherein said processing includes application of a wave-based algorithm that can map an angular location and a plurality of frequency parameters of said received scattered energy waves to construct images of said plaque and determine the risk of rupture and/or thrombosis, wherein said wave-based algorithm comprises a Hilbert space inverse wave (HSIW) algorithm.

14. The method of claim 13, further comprising measuring a fibrous collagen cap thicknesses of up to at least about 800 microns.

15. The method of claim 13, wherein at a predetermined angular imaging location, said receiver aperture is configured to receive up to 90-degrees of angular content resulting from said one or more radial scattered waves.

16. The method of claim 13, wherein said images are formed along a plane perpendicular to said longitudinal axis of rotation.

17. The method of claim 13, wherein said energy waves further comprise acoustic frequencies having a range between 20 MHz and 60 MHz.

18. A wave-based imaging apparatus, comprising:
a flexible substrate having a longitudinal axis and a distal region;
one or more elements disposed on said distal region, wherein each of said one or more elements is capable of directing one or more predetermined energy waves radially outward and wherein each of said one or more elements is capable of receiving one or more radial scattered energy waves from one or more objects; and
means for constructing images of said one or more objects from data obtained with said one or more elements, wherein said means embody a wave-based algorithm that can map an angular location and a plurality of frequency parameters of said received scattered energy waves, wherein said wave-based algorithm comprises a Hilbert space inverse wave (HSIW) algorithm.

19. The apparatus of claim 18, wherein said one or more elements comprise a plurality of fixed transducers arranged as an annular array, wherein each said transducer is capable of launching a primary field wave and a backscattered field wave is measured on all of remaining said transducers.

20. The apparatus of claim 18, wherein said one or more elements comprise a single rotating radially outward oriented transducer capable of rotating up to 360 degrees about said longitudinal axis.

21. The apparatus of claim 18, wherein said one or more elements comprise a single transmitting transducer and a receiver aperture further comprising a plurality of receiving transducers, wherein said transmitter and said receiver aperture are capable of rotating up to 360 degrees about said longitudinal axis.

22. The apparatus of claim 18, wherein said means contructs images along a plane perpendicular to said longitudinal axis of rotation.

23. The apparatus of claim 18, wherein said energy waves further comprise acoustic frequencies having a range between 100 Hz and 300 Hz.

24. The apparatus of claim 18, wherein said energy waves further comprise acoustic frequencies having a range between 20 MHz and 60 MHz.

25. The apparatus of claim 18, wherein said energy waves further comprise electromagnetic frequencies having a range between 100 KHz and 3 THz.

26. A wave-based imaging apparatus to characterize plaque, comprising:
a catheter having a longitudinal axis and a distal region;
a single transmitting transducer adapted to transmit energy waves and a receiver aperture further comprising a plurality of receiving transducers adapted to receive radial scattered energy waves, wherein said transmitter and said receiver aperture are disposed on said distal region and capable of rotating up to 360 degrees about said longitudinal axis; and
means for constructing intravascular tomography images from data obtained from said plurality of receiving transducers, wherein said means embody a Hilbert space inverse wave (HSIW) algorithm that can map an angular location and a plurality of frequency parameters of said received scattered energy waves.

27. The apparatus of claim 26, wherein a diameter of said distal region that comprises said transmitting transducer and said receiving aperture is between 0.25 millimeters and 5.00 millimeters, thereby enabling intravascular use.

28. The apparatus of claim 26, wherein said energy waves further comprise acoustic frequencies having a range between 20 MHz and 60 MHz.

29. The apparatus of claim 26, wherein said energy waves further comprise acoustic frequencies having a range between 100 Hz and 10 GHz.

30. The apparatus of claim 26, wherein said energy waves further comprise electromagnetic frequencies having a range between 1 kHz and 3 THz.

31. The method of claim 1, wherein said predetermined imaging mode utilizes a plurality of fixed transducers arranged as an annular array, wherein a transducer of said transducers launches a primary field wave and a backscattered field wave is measured on all of remaining said transducers.

* * * * *